(12) United States Patent
Chen

(10) Patent No.: US 9,808,526 B2
(45) Date of Patent: Nov. 7, 2017

(54) PHARMACEUTICAL KIT AND METHODS FOR CANCER TREATMENT VIA INTRACAVITY DELIVERY AND FOR PREPARING METAL NANOPARTICLE-ANTIBODY FRAGMENT CONJUGATE

(71) Applicant: Chieh Hsiao Chen, Taichung (TW)

(72) Inventor: Chieh Hsiao Chen, Taichung (TW)

(*) Notice: Subject to any disclaimer, the term of this patent is extended or adjusted under 35 U.S.C. 154(b) by 0 days.

(21) Appl. No.: 15/208,553

(22) Filed: Jul. 12, 2016

(65) Prior Publication Data

US 2016/0317659 A1 Nov. 3, 2016

Related U.S. Application Data

(62) Division of application No. 14/132,937, filed on Dec. 18, 2013, now Pat. No. 9,415,238.

(51) Int. Cl.
| | |
|---|---|
| *A61K 41/00* | (2006.01) |
| *A61K 39/00* | (2006.01) |
| *A61N 5/06* | (2006.01) |
| *A61K 47/48* | (2006.01) |
| *A61K 49/00* | (2006.01) |
| *C07K 16/28* | (2006.01) |
| *C07K 16/30* | (2006.01) |
| *A61N 5/067* | (2006.01) |

(52) U.S. Cl.
CPC .... *A61K 41/0052* (2013.01); *A61K 47/48607* (2013.01); *A61K 47/48861* (2013.01); *A61K 49/0008* (2013.01); *A61N 5/062* (2013.01); *C07K 16/2863* (2013.01); *C07K 16/3092* (2013.01); *A61K 2039/505* (2013.01); *A61N 2005/067* (2013.01); *A61N 2005/0662* (2013.01); *A61N 2005/0663* (2013.01)

(58) Field of Classification Search
None
See application file for complete search history.

(56) References Cited

U.S. PATENT DOCUMENTS

| 2006/0057623 A1 | 3/2006 | Yeh |
| 2013/0034854 A1 | 2/2013 | Ashworth-Sharpe et al. |

OTHER PUBLICATIONS

Arruebo et al. "Antibody-Conjugated Nanoparticles for Biomedical Applications" Journal of Nanomaterials (2009), vol. 2009, Article ID 439389, pp. 1-24.*
Ijeh "Covalent gold nanoparticle-antibody conjugates for sensitivity improvement in LFIA" A dissertation submitted to the Mathematics, Informatics and Natural Sciences Faculty of Hamburg University, Dec. 2011, pp. 1-139.*
Arruebo et al.."Antibody-Conjugated Nanoparticles for Biomedical Applications" Journals of Nanomaterials (2009), vol. 2009, Article ID 439389, pp. 1-24.
Ijeh "Covalent gold nanoparticle-antibody conjugates for sensitivity improvement in LIFA" A dissertation submitted to the Mathematics, Informatics and Natural Sciences Faculty of Hamburg University, Dec. 2011, pp. 1-139.

* cited by examiner

*Primary Examiner* — Carlos Azpuru
*Assistant Examiner* — Casey Hagopian
(74) *Attorney, Agent, or Firm* — Haverstock & Owens LLP

(57) ABSTRACT

The present invention provides a pharmaceutical kit, methods for cancer treatment and for preparing a metal nanoparticle-antibody fragment conjugate, which can reduce the recurrence rate of cancer and provide a safer and less invasive therapeutic method for cancer treatment.

7 Claims, 5 Drawing Sheets

PHARMACEUTICAL KIT AND METHODS FOR CANCER TREATMENT VIA INTRACAVITY DELIVERY AND FOR PREPARING METAL NANOPARTICLE-ANTIBODY FRAGMENT CONJUGATE

RELATED APPLICATION(S)

The present application is a divisional of co-pending U.S. patent application Ser. No. 14/132,937, filed Dec. 18, 2013, and entitled "PHARMACEUTICAL KIT AND METHODS FOR CANCER TREATMENT VIA INTRACAVITY DELIVERY AND FOR PREPARING METAL NANOPARTICLE-ANTIBODY FRAGMENT CONJUGATE" which is hereby incorporated by reference.

BACKGROUND OF THE INVENTION

1. Field of the Invention

The present invention relates to a pharmaceutical kit, methods for cancer treatment via intracavity delivery and for preparing a metal nanoparticle-antibody fragment conjugate.

2. Description of Related Art

In recent years, surface plasmonic nanoparticles have been commonly used due to the unique and tunable optical properties. The wavelength absorbed by nanoparticles depends on their size and shape. Many researches have been conducted on the application of gold nanoparticles (GNPs) in cancer diagnosis or therapy because GNPs have excellent photothermal properties, such as surface plasmon resonance, biological compatibility, and etc. Surface plasmonic gold nanoparticles have been proved to be more nontoxic than other kinds of nanoparticles for cancer treatment and detection, such as core-shell nanoparticles, magnetic nanoparticles and quantum dots where silica is commonly used in the cores thereof. In addition, GNPs are characterized by high chemical stability, high affinities to biomolecules, and non-cytotoxicity, and can be used as agents for cancer detection and therapy.

On these grounds, GNPs including gold nanorods and gold/silica nanoshells have been recently used as both imaging and therapy agents for treating a number of cancers, such as breast cancer, brain tumor, oral cavity cancer and prostate cancer with similar absorption wavelengths of near infrared (NIR). For the examination of cell uptake, GNPs with a spherical shape and a diameter of 50 nm have the best uptake capacity for mammalian cells compared with those of other sizes (14, 30, 74, and 100 nm) or shapes (e.g. a rod shape) (40×14 nm and 74×14 nm). Thermal therapies cause necrosis in cancer cells by rupturing membranes and releasing digestive enzymes. Currently, a variety of heat sources, such as ultrasound, microwaves, and laser light in thermal therapy, have been employed.

Although various hyperthermia techniques have been widely employed in treating cancers, such techniques involve heating tissues along the course and are likely to cause damages to normal tissues due to the lack of specificity of the heating. The aforementioned cancers often develop from cells on the inner surfaces of the organs. In such cases, a doctor sometimes resects the carcinoma only rather than the entire organ to maintain the function of the organ. Unfortunately, the recurrence rate may increase due to the foregoing operation, and thus an adjuvant therapy is required to reduce the recurrence rate. For example, bladder carcinoma is a relatively common malignancy in the urinary tract. There are more than 90% of bladder carcinoma patients have primary transitional cell carcinoma (TCC) in their bladders. A doctor sometimes resects the carcinoma only (e.g. transurethral resection of bladder tumor (TUR-BT) for superficial urinary bladder cancer) rather than the entire organ to maintain the function of the organ. However, the recurrence rate of urinary bladder cancer is about 70% in 5 years after the TUR-BT operation, and an adjuvant therapy, such as intravesical Bacillus Calmette-Guerin (BCG) or chemotherapy agent instillation, is required to reduce the recurrence rate. The problem is these agents have very limited effect on the recurrence and often have environmental toxicities.

BCG is a potent intravesical therapy for superficial (non-invasive) bladder cancers, but the recurrence rate is still high. Although intravesical adjuvant therapies, such as BCG, Mitomycin-C (MMC), Epirubicin or the like, have been used in clinical practice, the recurrence rate is close to 50% (40% and 53% in BCG and chemotherapy, respectively) while the disease progression rate is 15% in the test groups. These results show poor therapeutic effect with less benefit. Moreover, patients may be reluctant to take these adjuvant therapies due to certain side effects, such as cystitis, fever, haematuria, or high urinary frequency.

SUMMARY OF THE INVENTION

In order to solve the aforementioned problem, the present invention provides a pharmaceutical kit, a method for cancer treatment via intracavity delivery. The present invention involves delivering the modified nanoparticles to the cavity of an organ and utilizing specific optical or magnetic features, such as photothermal effect, to kill transitional cell carcinomas (TCC) by exposing them to a green light laser. The present invention not only reduces the high recurrence rate of TCC, but also avoids the side effects of traditional chemotherapy.

To achieve the foregoing objects, the present invention provides a pharmaceutical kit for cancer treatment via intracavity delivery, comprising: (a) a metal nanoparticle-antibody fragment conjugate; and (b) a spherical or superficial green light laser system; wherein the metal nanoparticle is modified with carboxyl group or PEG and covalently bound to the antibody fragment comprising sulfhydryl group, and the green light laser system is provided to irradiate the metal nanoparticle-antibody fragment conjugate bonded to the cancer cell.

In addition, the present invention provides a method for cancer treatment via intracavity delivery, comprising the steps of: (a) preparing a metal nanoparticle-antibody fragment conjugate, wherein the metal nanoparticle is modified with carboxyl group or PEG and covalently bound to the antibody fragment comprising a sulfhydryl group; (b) administering the conjugate to a cancer cell; and (c) providing a spherical or superficial green laser light source to irradiate the metal nanoparticle-antibody fragment conjugate bonded to the cancer cell.

Furthermore, the present invention also provides a method for preparing a metal nanoparticle-antibody fragment conjugate where the conjugate is irradiated by a spherical or superficial green laser light source to treat a cancer, comprising the steps of: (a) preparing a metal nanoparticle modified with carboxyl group or PEG; (b) providing an antibody; (c) cleaving the antibody by a reagent to form an antibody fragment having sulfhydryl group; and (d) forming the conjugate by conjugating the metal nanoparticle with the antibody fragment.

In a preferred embodiment of the present invention, the antibody fragment is a half-antibody fragment.

In a preferred embodiment of the present invention, the antibody fragment is a monoclonal antibody fragment.

In a preferred embodiment of the present invention, a diameter of the metal nanoparticle ranges from 30 to 60 nm.

In a preferred embodiment of the present invention, a diameter of the metal nanoparticle ranges from 60 to 100 nm.

In a preferred embodiment of the present invention, a diameter of the metal nanoparticle is more than 100 nm.

In a preferred embodiment of the present invention, the metal nanoparticle is a gold or iron nanoparticle.

In a preferred embodiment of the present invention, the conjugate is used to treat a transitional cell carcinoma.

In a preferred embodiment of the present invention, the reagent is 2-mercaptoethylamine.

In a preferred embodiment of the present invention, the green laser light source has a wavelength ranging from 500 to 600 nm.

This summary is not an extensive overview of the disclosure and its sole purpose is to present some concepts disclosed herein in a simplified form as a prelude to the more detailed description that is presented later.

Many of the attendant features and advantages of the present invention will be better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
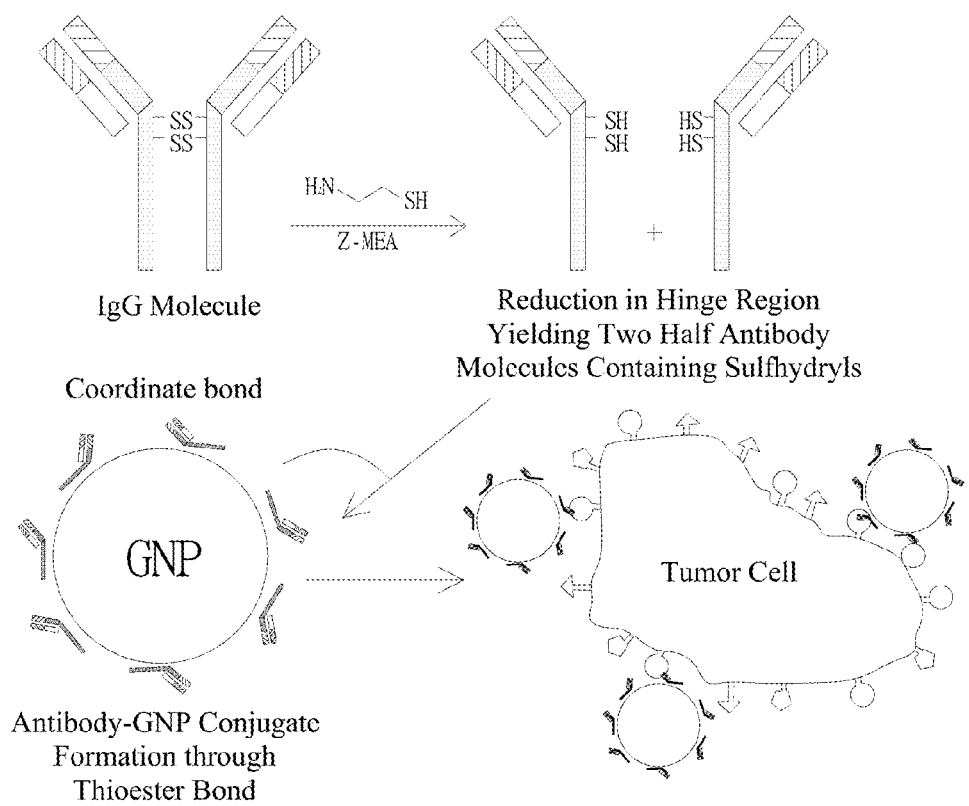
FIG. 1 illustrates the cleaving of disulfide bonds and the formation of half-antibodies for the conjugation with GNPs.

Details of the objects, technical configuration, and effects of the present invention will be described more fully hereinafter with reference to the accompanying drawings, in which exemplary embodiments of the invention are shown.

The like reference numerals indicate the like configuration throughout the specification, and in the drawings, the length and thickness of layers and regions may be exaggerated for clarity. The technical content of the present invention will become apparent by the detailed description of the following embodiments and the illustration of related drawings as follows. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Various embodiments will now be described more fully with reference to the accompanying drawings, in which illustrative embodiments are shown. The inventive concept, however, may be embodied in different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The singular forms "a," and "the" are used herein to include plural referents unless the context clearly dictates otherwise.

The term "half-antibody fragment" defined in the present invention includes antibodies in which, the inter-heavy chain disulfide bond(s) are absent such that a single light chain polypeptide and a single heavy chain polypeptide are unconnected to the corresponding single light chain polypeptide and single heavy chain polypeptide and form a half-antibody with a sulfhydryl group.

As used herein, the term "superficial" in the present invention is defined as relating to the surface or near-surface of the cancer cells, such as superficial bladder cancer in the case of early bladder cancer. Hence, the superficial green laser light refers to the light placed near the surface of the cancer cells.

One object of the present invention is to solve the problem of a high recurrence rate in conventional cancer therapies. Furthermore, the present invention provides methods for cancer treatment via intracavity delivery and for preparing a metal nanoparticle-antibody fragment conjugate where the conjugate is irradiated by a spherical or superficial green laser light source to treat a cancer according to the needs in the clinical practice. The method employs the modified nanoparticles delivered into the cavity of an organ and utilizes specific optical or magnetic features, such as photothermal, photodynamic, Raman spectrum, phtoacoustic or magnetic field effects, to diagnose and/or treat cancers.

To achieve the aforementioned objects, the present invention provides a pharmaceutical kit for cancer treatment via intracavity delivery, comprising: (a) a metal nanoparticle-antibody fragment conjugate; and (b) a spherical or superficial green light laser system; wherein the metal nanoparticle is modified with carboxyl group or PEG and covalently bound to the antibody fragment comprising sulfhydryl group, and the green light laser system is provided to irradiate the metal nanoparticle-antibody fragment conjugate bonded to the cancer cell.

In addition, the present invention provides a method for cancer treatment via intracavity delivery, comprising the steps of: (a) preparing a metal nanoparticle-antibody fragment conjugate, wherein the metal nanoparticle is modified with carboxyl group or PEG and covalently bound to the antibody fragment comprising a sulfhydryl group; (b) administering the conjugate to a cancer cell; and (c) providing a spherical or superficial green laser light source to irradiate the metal nanoparticle-antibody fragment conjugate bonded to the cancer cell.

Furthermore, the present invention provides a method for preparing a metal nanoparticle-antibody fragment conjugate where the conjugate is irradiated by a spherical or superficial green laser light source to treat a cancer, comprising the steps of: (a) preparing a metal nanoparticle modified with carboxyl group or PEG; (b) providing an antibody; (c) cleaving the antibody by a reagent to form an antibody fragment having sulfhydryl group; and (d) forming the conjugate by conjugating the metal nanoparticle with the antibody fragment.

The following examples are provided to elucidate certain aspects of the present invention and to aid those skilled in the art in practicing this invention. These examples are exemplary and not intended to limit the scope of the invention in any manner.

EXAMPLE 1

Bladder Tumor Cells Culture

The malignant urothelial cell lines (UCC), MBT-2 (Murine) T24, 9202 and 8301 (Human) were cultured at 37° C. at an atmospheric pressure. The culture medium of Roswell Park Memorial Institute 1640 (Gibco-BRL) contains 10% fetal bovine serum and 1% penicillin-streptomycin. It should be noted that the bladder tumor cell incubated in this embodiment is exemplary, and any other tumor cell of the genitourinary, such as a transitional cell carcinoma cell, can be used in the present invention.

EXAMPLE 2

Preparation of Gold Nanoparticles (GNPs)

GNPs were prepared by reducing gold from chloroauric acid according to the method developed by Turkevich et al. (Kimling J, Maier M, Okenve B et al. (2006) Turkevich Method for Gold Nanoparticles Synthesis Revisited J Phys Chem B 110:15700-15707). In brief, hydrogen tetrachloroaurate (III) trihydrate (Sigma) was diluted with D.D. water (Millipore) to a final concentration of $1.0 \times 10^{-3}$ M. Next, $34.6 \times 10^{-3}$ M trisodium citrate (J. T. Baker) was added to the boiling gold chloroauric acid solution and vigorously stirred until complete dispersion. When the solution's color turned to purplish red, the solution containing gold nanoparticles formed therein was removed from the heat source and left to cool at room temperature for at least 30 min. The particle suspension solution containing gold nanoparticles was centrifuged and then the collected particles were diluted with $20 \times 10^{-3}$ M HEPES buffer (pH 7.4, Sigma) to a final concentration of 0.8 optical density at 500-600 nm, preferably at 532 nm. The collected particles were finally filtered with a Millipore filter of 0.22 μm to ensure a better sterility.

However, this embodiment relating to the preparation of gold nanoparticles is exemplary and is not intended to limit the scope of the present invention. For example, iron nanoparticles can also be prepared and used in the present invention. Furthermore, for different purposes, metal nanoparticles may have a diameter of from 30-60 nm, 60-100 nm, to greater than 100 nm. Preferably, PEG with high affinity to GNPs is used to modify GNPs because it can block the antibody to link GNPs. In addition, GNPs can be modified with a carboxyl group for the same purpose.

EXAMPLE 3

Semi Anti-EGFR and Anti-Mucin7 Antibody Labeled GNPs

In order to enhance the conjugation between GNPs and antibody, antibody fragments, such as half-antibody fragments, were adopted. As GNPs have high affinity to a sulfhydryl group, they can readily combine with the half-antibody molecules produced through reduction, as shown in FIG. 1.

The steps of reducing antibodies follow the works of Mahnke et al (Mahnke K, Qian Y, Knop J et al. (2003) Introduction of CD4+/CD25+ regulatory T cells by targeting of antigens to immature dendritic cells. Blood 101:4862-4869). The antibody was dissolved in 20 mM sodium phosphate buffer (pH 7.5) with 150 mM NaCl and 10 mM ethylene diamine tetraacetic acid (EDTA) at a concentration of 10 mg/ml. Next, 6 mg of 2-mercaptoethylamine (2-MEA) was added to the antibody solution.

After the antibody was dissolved, the reaction mixture was incubated at 37° C. for 90 min. At the final stage, the reduced antibody was purified by a gel filtration column equilibrated with the same buffer containing 5 mM EDTA and thereby to remove excess 2-MEA. The dialysis buffer was changed twice to ensure that the desalted antibody was purified. It is to be noted that anti-EGFR and anti-Mucin7 antibody used in this embodiment are exemplary and not intended to limit the scope of the present invention, and that most monoclonal antibodies can be employed in the present invention.

EXAMPLE 4

GNPs/Cell Carcinoma Incubation and Laser Therapy Experiment

The immunoglobulin G (IgG) conjugated GNPs were added to the aforementioned urinary bladder carcinoma cell lines plated in a 6-well tissue culture plate with 1 cc per well. After being incubated at 37° C. for 30 min, the cell/anti-EGER/Au were washed three times to remove the unbounded suspension. The green light laser system (IDAS) having a wavelength of 532 nm provides a stable and safe power in this embodiment. The wavelength is overlapped with the GNPs absorption region to promote the thermal efficiency. The pulse mode was used to prevent the medium from being overheated. In addition, the green laser light source is preferably a spherical or superficial green laser light source.

After being incubated for 30 min, the cell lines which immersed in GNPs suspension were exposed to the 532 nm laser light source at various power densities for 500 times. The cell images were taken using Motic AE21 microscope under 40× magnification to observe the viability of the cell stained with 0.4% trypan blue (Sigma).

EXAMPLE 5

Orthotopic Bladder Cancer Animal Model

In order to verify the effectiveness of the therapy, an animal study is required. The urinary bladder cancer model developed by Xiao et al (Xiao Z, McCallum T J, Brown K M et al. (1999) Characterization of a novel transplantable orthotopic rat bladder transitional cell tumor model. Br J Cancer 81:638-646) was adopted. In this embodiment, Crede's method was performed to evacuate urine after a C3H mouse was anaesthetized. The mouse bladder was then catheterized with a 24-gauge plastic cannula applied with an inert lubricant for seeding agents. The bladder mucosa was destroyed with 0.1 N of hydrochloric acid (HCl) and neutralized by 0.1 N of potassium hydroxide (KOH). After 15 seconds elapsed, the bladder was rinsed with sterile phosphate-buffered saline (PBS).

$1 \times 10^6$ MBT-2 cells were inoculated into the mouse via the urethra for tumor seeding immediately after bladder instillation. In order to evaluate the tumor progression, mice were sacrificed to examine the organ sections every fortnight post-inoculation.

RESULTS AND DISCUSSION

Figure 2:
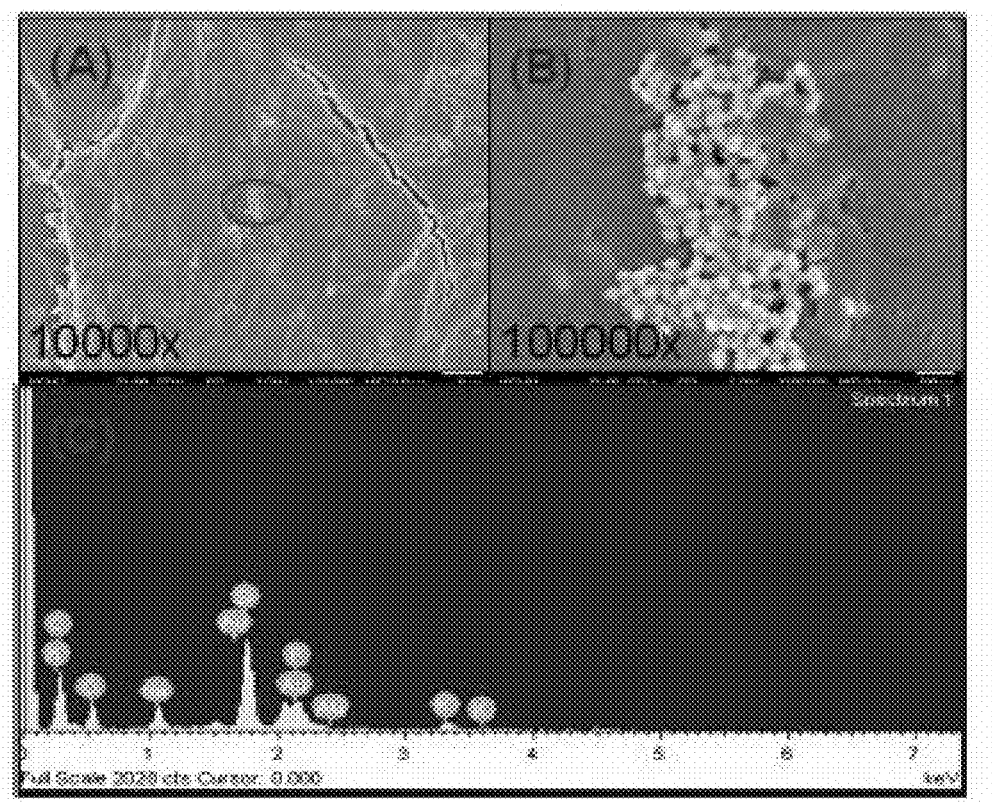
FIG. 2 illustrates scanning electron microscope (SEM) images (A) and (B), which are taken at different magnifications (10000× and 100000×) and show the existence of semi anti-epidermal growth factor receptor (EFGR)/GNPs, and a graph (C) showing the Scanning Electron Microscopy-Energy Dispersive Spectroscopy (SEM-EDS) analysis of Au distribution of MBT-2 cells.

In order to confirm the existence of semi anti-EFGR/GNPs, scanning electron microscope (SEM) and transmission electron microscopy (TEM) were used in the present invention to observe the distribution of GNPs. As shown in the SEM images in FIG. 2, the semi anti-EFGR/GNPs bonded with the MBT-2 cells in numerous parts. The weight of Au contains 5.36% by weight of total elements, which proved the existence of GNPs.

Figure 3:
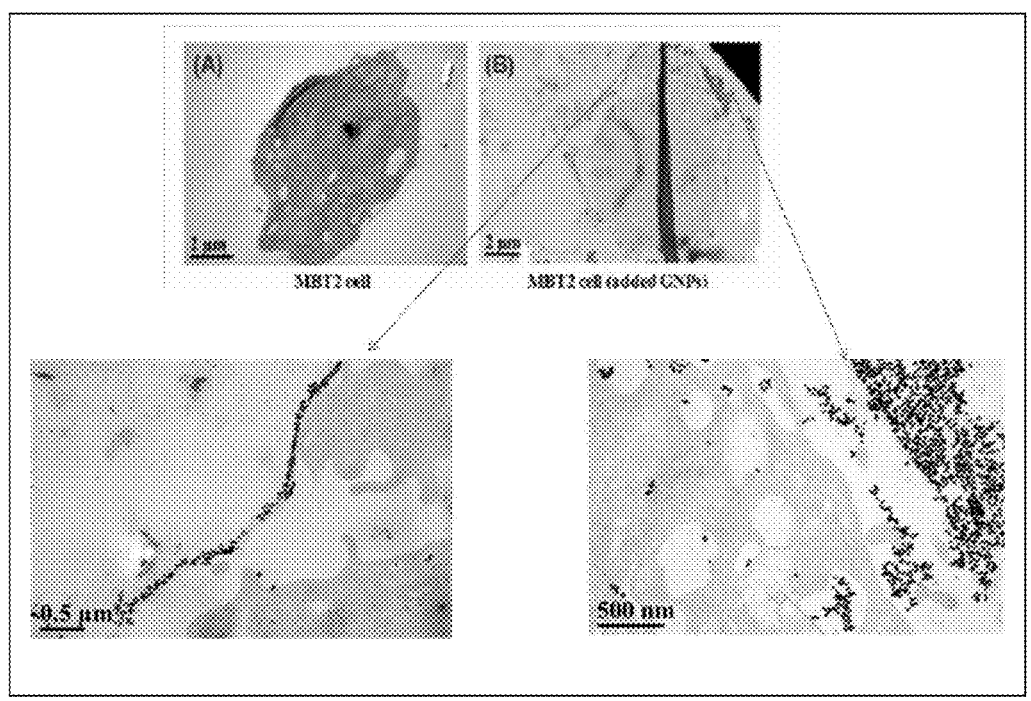
FIG. 3 illustrates a transmission electron microscopy (TEM) image (A) of MBT-2 cell lines, and TEM image (B) of MBT-2 cell lines added with semi anti-EFGR/GNPs, and the partial enlargement of (B)

Referring to FIG. 3, the TEM images also show the existence of semi anti-EFGR/GNPs. It is found that there is a small amount of cellular uptake of nanoparticles through endocytosis. GNPs have potential to enter tumors because of the size-dependent effects thereof and thereby to enhance the treatment for cancer.

Figure 4:
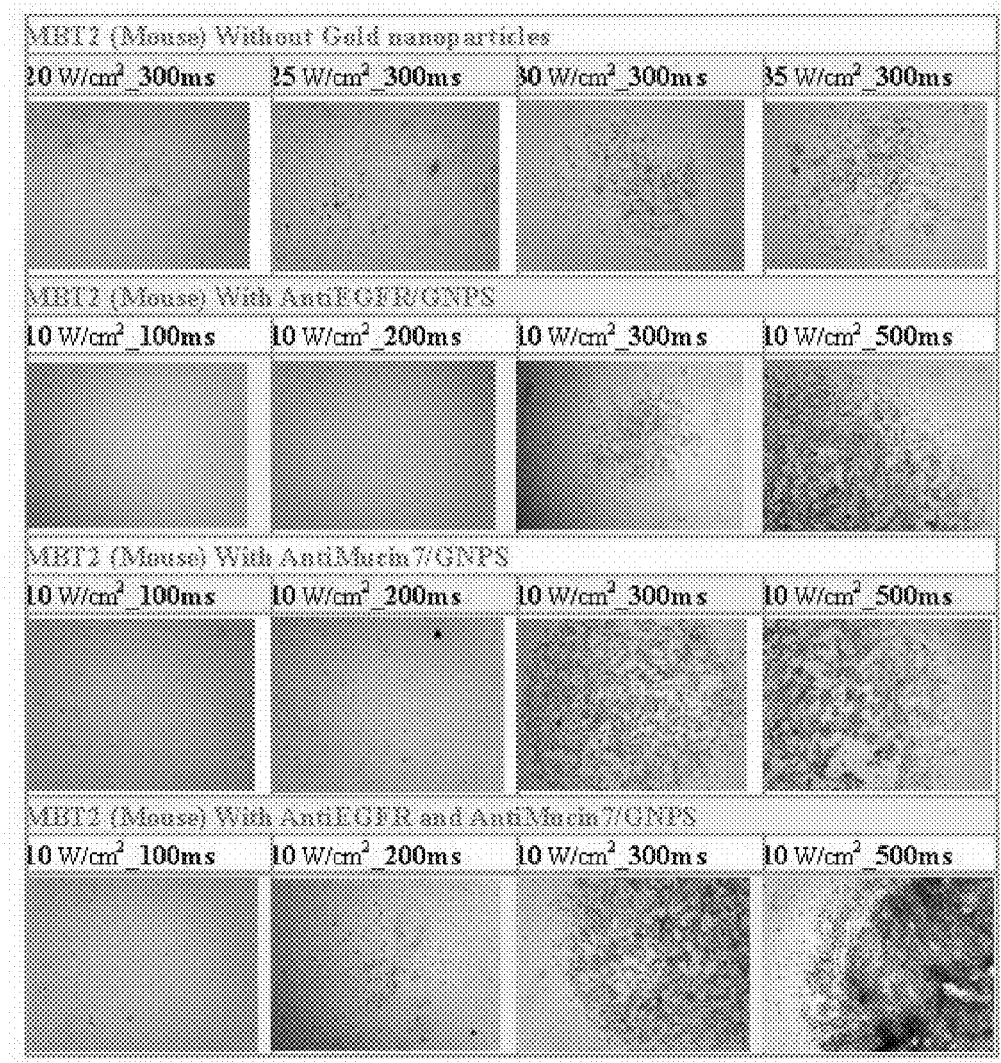
FIG. 4 shows damages caused to MBT-2 cells undergoing laser treatment with different conditionings.

For the laser experiment, different kinds of transitional cell carcinomas (TCC)(MBT2, T24, 9202, 8301) cell lines were tested. After metal nanoparticles absorbed the energy of light, the surface electrons would oscillate and polarize in order to against any change in the external electromagnetic field. A specific optical feature, such as photothermal effect, was employed to kill transitional cell carcinomas by exposing them to a green laser light source which is spherical or superficial. This laser light source can scatter the energy of light all over the surface of cancer cells, such that the gold nanoparticles absorbed appropriate energies to kill cancer cells in case the excessive energy hurts benign cells. Thus, the antibodies work as the aiming system of the bombs, the gold nanoparticles, which can destroy the cell membrane of the cancer cells when it was exposed to spherical or superficial green light in selected wavelength. Furthermore, it can quickly target the tumor. Cancer cells added with semi antibody/GNPs were damaged at a relatively lower energy (10 W/300 ms) compared with those without being added with semi antibody/GNPs which were damaged at 30 W/300 ms, as shown in FIG. 4. Furthermore, the combination of two kinds of antibody/GNPs enables more effective targeting of tumors and improves the treatment effect.

Figure 5:
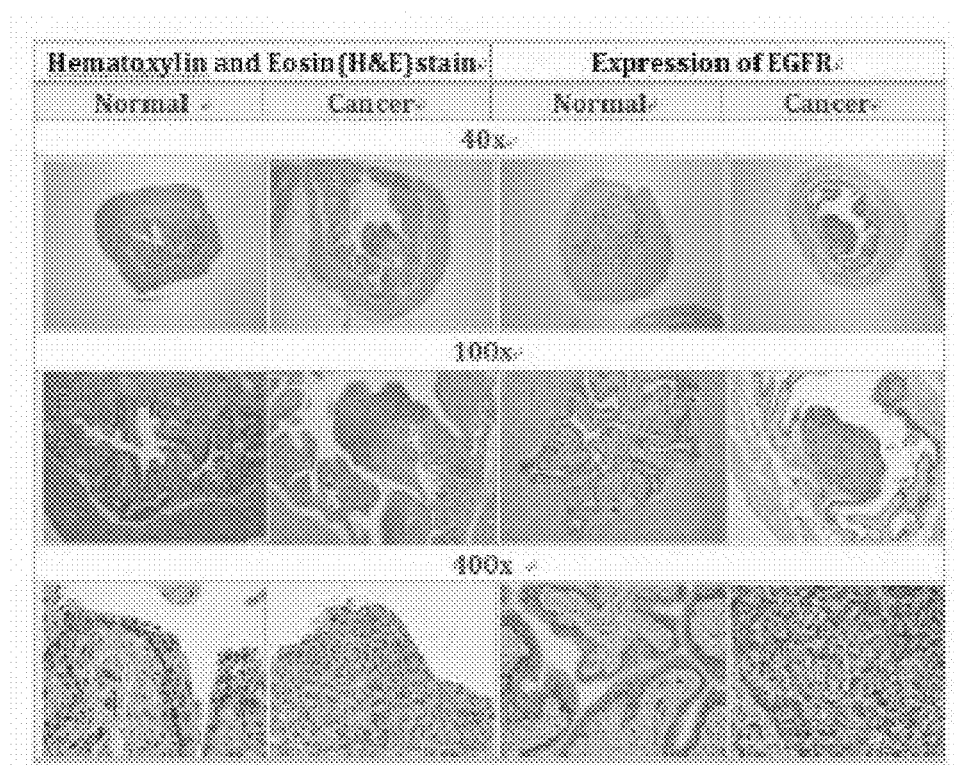
FIG. 5 illustrates images of histological sections of C3H mice bladder tumors at different magnifications (40×, 100×, and 100000×); it is to be noticed that the arrangement of epidermal cells and nuclear contours are irregular (excessive proliferation of tumor cells).

To verify the orthotopic bladder cancer model, histological sections were obtained, as shown in FIG. 5. The results show the formation of tumors in the bladder lumens with EFGR over expression. Most important of all, all the tumors are superficial (non-invasive). For a superficial bladder cancer (i.e. early bladder cancer), an adjuvant intravesical therapy is the most suitable treatment option.

To sum up, antibodies combined with GNPs can target at a specific area of a cell membrane. Therefore, the amount of laser power used to damage cancer cells can be reduced by about half when GNPs are added. The overlapping wavelength between GNPs and laser will produce stronger thermal energy and consequently improve the effectiveness of cancer treatment.

In accordance with the present invention, the conjugate for cancer treatment, and the methods for preparing the conjugate and cancer treatment have the following advantages:

(1) The methods mentioned above can be used to diagnose and treat cancers and/or to prevent the recurrence thereof. They can be used alone or as adjuvant therapies.

(2) The use of GNPs, rods or spheres, which have a diameter of 30-60 nm, 60-100 nm, or greater than 100 nm and are conjugated with modified antibodies, such as half-antibodies, in the treatment for human organs in different purposes is a potential use of agents.

(3) The use of optical features in therapies, such as photothermal therapy, to deliver a diffused or focused green light source having a specific wavelength (532 nm) absorbed by nanoparticles is unique.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for cancer treatment via intracavity delivery, comprising the steps of:
    a) preparing a metal nanoparticle-antibody fragment conjugate, wherein the metal nanoparticle is modified with carboxyl group or polyethylene glycol (PEG) and covalently bound to the antibody fragment comprising sulfhydryl group, wherein said antibody fragment is one of a half-antibody fragment and a monoclonal antibody fragment;
    b) administering the conjugate to a cancer cell; and;
    c) providing a spherical or superficial green laser light source to irradiate the metal nanoparticle-antibody fragment conjugate bonded to the cancer cell.

2. The method of claim 1, wherein a diameter of the metal nanoparticle ranges from 30 to 60 nm.

3. The method of claim 1, wherein a diameter of the metal nanoparticle ranges from 60 to 100 nm.

4. The method of claim 1, wherein a diameter of the metal nanoparticle is more than 100 nm.

5. The method of claim 1, wherein the metal nanoparticle is a gold or iron nanoparticle.

6. The method of claim 1, wherein the green laser light source has a wavelength from 500 to 600 nm.

7. The method of claim 1, wherein the conjugate is used to treat a transitional cell carcinoma.

* * * * *